United States Patent
Lin et al.

(10) Patent No.: US 12,097,195 B2
(45) Date of Patent: Sep. 24, 2024

(54) PHARMACEUTICAL COMPOSITION CONTAINING ALKYNYL COMPOUND AND PREPARATION METHOD AND APPLICATION THEREOF

(71) Applicants: ASCENTAGE PHARMA (SUZHOU) CO., LTD., Suzhou (CN); ASCENTAGE PHARMA GROUP CORP LIMITED, Hong Kong (CN); Guangzhou Healthquest Pharma Co., Ltd., Guangdong (CN)

(72) Inventors: Yanqiong Lin, Suzhou (CN); Jianfeng Wen, Suzhou (CN); Feng Xu, Suzhou (CN); Jiaan Huang, Suzhou (CN); Shixiong Li, Suzhou (CN); Xiaoling He, Suzhou (CN); Shihe Liang, Suzhou (CN)

(73) Assignees: Ascentage Pharma (Suzhou) Co., Ltd. (CN); Ascentage Pharma Group Corp Limited (CN); Guangzhou Healthquest Pharma Co., Ltd. (CN)

( * ) Notice: Subject to any disclaimer, the term of this patent is extended or adjusted under 35 U.S.C. 154(b) by 107 days.

(21) Appl. No.: 17/259,719

(22) PCT Filed: Dec. 9, 2019

(86) PCT No.: PCT/CN2019/124024
§ 371 (c)(1),
(2) Date: Jan. 12, 2021

(87) PCT Pub. No.: WO2021/114020
PCT Pub. Date: Jun. 17, 2021

(65) Prior Publication Data
US 2022/0296587 A1    Sep. 22, 2022

(51) Int. Cl.
*A61K 31/496* (2006.01)
*A61K 9/20* (2006.01)
*A61K 9/48* (2006.01)

(52) U.S. Cl.
CPC .......... *A61K 31/496* (2013.01); *A61K 9/2054* (2013.01); *A61K 9/4866* (2013.01)

(58) Field of Classification Search
CPC .................................................... A61K 31/496
See application file for complete search history.

(56) References Cited

U.S. PATENT DOCUMENTS 8,846,671 B2 * 9/2014 Ding ................... C07D 471/04
514/233.2

FOREIGN PATENT DOCUMENTS

| CN | 101885722 A | 11/2010 |
|---|---|---|
| CN | 102770129 A | 11/2012 |
| CN | 104341425 A | 2/2015 |
| CN | 107233325 A | 10/2017 |
| CN | 110917157 A | 6/2020 |
| WO | 201995854 A1 | 10/2019 |
| WO | WO 2020/114348 A1 * | 6/2020 |

OTHER PUBLICATIONS

Niazi, Handbook of Pharmaceutical Manufacturing Formulations, vol. 1, Chapters 1 and 2, (72 pages), 2004.*
ISR for PCT/CN2019/124024 dated Sep. 18, 2020 (8 pgs).

* cited by examiner

*Primary Examiner* — Deepak R Rao
(74) *Attorney, Agent, or Firm* — Honigman LLP; Lucy X. Yang; Jonathan P. O'Brien

(57) ABSTRACT

The present invention relates to a pharmaceutical composition containing alkynyl compound, a preparation method thereof and its application. The present invention discloses a pharmaceutical composition comprising an active pharmaceutical ingredient and an available pharmaceutical excipient; The active pharmaceutical ingredient is 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide, or its pharmaceutical acceptable salt; The available pharmaceutical excipients includes diluents and lubricants. The pharmaceutical composition can effectively improve the bioavailability of the alkynyl compound, has good dissolution and stability, and improve the drug safety.

18 Claims, No Drawings

PHARMACEUTICAL COMPOSITION CONTAINING ALKYNYL COMPOUND AND PREPARATION METHOD AND APPLICATION THEREOF

TECHNOLOGY FIELD

The present invention relates to the field of pharmaceutical preparations, especially relates to a pharmaceutical composition containing alkynyl compound, its preparation method and application.

BACKGROUND ART

The alknyl compound involved in the present invention was first recorded in CN101885722A, and its structure is 3-((1H-pyrazolo[3,4-b]pyridin-5-yl)ethynyl)-4-methyl-N-(4-((4-methylpiperazin-1-yl)methyl)-3-(trifluoromethyl) phenyl)-benzamide. The compound is a new oral biological effective Bcr-Abl inhibitor which can effectively treat tumors and blood system diseases, especially for chronic leukemia K562 and acute leukemia MOLT with very good inhibition rate. The alknyl compound can effectively target broad-spectrum expression drug mutation including T3151. As a Bcr-Abl inhibitor, it is a very effective candidate drug and thereof can effectively overcome the resistance of Imatinib. Therefore, it has attracted wide attention of numerous pharmaceutical companies.

At present, there are no reports of pharmaceutical composition containing the alkynyl compound, especially a pharmaceutical composition containing alkynyl compounds with good stability and high dissolution, which can be used for patients. Considering that the alkynyl compound has a good clinical prospect, it is urgent to develop a composition containing alkynyl compound with good dissolution and stability, which greatly facilitates clinical use of the alkynyl compound and benefits the majority of patients.

SUMMARY OF THE INVENTION

The present invention provides a pharmaceutical composition containing alkynyl compound, and its preparation method and application thereof. The pharmaceutical composition can effectively improve the bioavailability of the alkynyl compound, has good dissolution and stability, and improve the drug safety. The alkynyl compound can be in the form of a free base or a pharmaceutically acceptable salt.

The present invention provides a pharmaceutical composition comprising active pharmaceutical ingredients and available pharmaceutical excipients. Said pharmaceutical active ingredient is 3-((1H-pyrazolo[3,4-b]pyridin-5-yl) ethynyl)-4-methyl-N-(4-((4-methylpiperazin-1-yl)methyl)-3-(trifluoromethyl)phenyl)-benzamide, or its pharmaceutically acceptable salt thereof. The available pharmaceutical excipients include diluents and lubricants.

In the present invention, the amount of the pharmaceutical active ingredient is preferably from 0.5 to 15 by weight, more preferably from 1 to 14.5 (for example, 1.4, 3, 3.3, 13, 13.3, 14 or 14.3).

In the present invention, the diluents can be the conventional diluents in the field, preferably including but not limited to one or more of calcium hydrogen phosphate, kaolin, dextrin, lactose, sucrose, microcrystalline cellulose, powdered cellulose, calcium carbonate, sorbitol powder, starch, starch derivatives, erythritol, xylitol and fructose, preferably one or more of dextrin, lactose, microcrystalline cellulose and starch, more preferably one or more of dextrin, lactose and microcrystalline cellulose, further preferably microcrystalline cellulose (such as microcrystalline cellulose PH102). The starch derivatives can be the conventional starch derivatives in the field, preferably including one or more of corn starch, potato starch, compressible starch, modified starch and pregelatinized starch.

In the present invention, the dosage of the diluent can be the conventional dosage in the field. By weight, the amount of the diluent is preferably from 10 to 98, more preferably from 20 to 98, further preferably from 59 to 98, and further preferably from 80 to 98 (for example, 84, 84.2, 85.7, 86, 95.7, 96, 96.7 or 97).

In the present invention, the lubricants can be the conventional lubricants in the field, preferably including but not limited to one or more of magnesium stearate, stearic acid, calcium stearate, zinc stearate, liquid paraffin wax, polyethylene glycol (peg), silica, colloidal silica, siliciidoxydum, talcum powder, starch, and hydrogenated vegetable oil, more preferably one or more of magnesium stearate, stearic acid, calcium stearate, siliciidoxydum and talcum powder in the powder of one or more of the following, more preferably one or more of magnesium stearate, stearic acid, calcium stearate and siliciidoxydum in one or several, further preferably magnesium stearate.

In the present invention, the dosage of the diluent can be the conventional dosage in the field. The dosage of the lubricants preferably from 0.1 to 5 and further from 0.5 to 3 (for example, 0.5 or 1) by weight.

In the present invention, the available pharmaceutical excipients can also include disintegrating agents. The disintegrating agents can be the conventional disintegrating agents in the field, preferably including but not limited to one or more of low-substituted hydroxypropyl cellulose, crosslinked polyvingypyrrolidone, crosslinked carboxymethyl starch sodium, sodium carboxymethyl starch and croscarmellose sodium, more preferably one or more of low-substituted hydroxypropyl cellulose, crosslinked polyvingypyrrolidone, crosslinked carboxymethyl starch sodium and croscarmellose sodium, more preferably croscarmellose sodium.

In the present invention, the dosage of the disintegrating agent can be the conventional dosage in the field. The dosage of the disintegrating agents preferably from 0.5 to 20, from 0.5 to 10 and from 0.5 to 3 by weight (for example, 1).

In the present invention, the available pharmaceutical excipients can also include adhesives, the adhesive can be the conventional adhesives in the field, preferably including but not limited to one or more of hydroxypropyl cellulose, hydroxypropyl methyl cellulose, polyvinylpyrrolidone, polyvinyl alcohol, arabic gum, alginic acid, sodium alginate and gelatin, more preferably one or more of hydroxypropyl cellulose, hydroxypropyl methyl cellulose, polyvinylpyrrolidone and polyvinyl alcohol, more preferably hydroxypropyl cellulose and/or polyvinylpyrrolidone.

In the present invention, the dosage of the adhesives can be the conventional dosage in the field. The dosage of the adhesives is preferably from 0.1 to 5, more preferably from 0.5 to 3.

In the present invention, the available pharmaceutical excipients can also include wetting agents, the wetting agents can be the conventional wetting agents in the field, preferably including but not limited to one or more of polysorbates, polyoxyethylene aliphatic alcohol ethers, polyoxyethylene castor oils, phospholipids, hydrosulfates and poloxamer, more preferably sodium lauryl sulfate.

In the present invention, the dosage of the wetting agents can be the conventional dosage in the field. The dosage of the wetting agents preferably from 0 to 10, but not 0, more preferably from 0.1 to 10.

In the present invention, the available pharmaceutical excipients can also include food additives, the food additives can be the conventional food additives in the field, preferably including but not limited to one or more of preservatives, antioxidants, color fixatives, bleaches, acidulants, coagulants, bulking agents, thickeners, defoaming agents, sweetening agents, coloring agents, emulsifiers, quality modifiers, anti-caking agents, palatability enhancers, enzyme preparations, coating agents, foaming agents, antistaling agents, flavours and nutrition enhancers, more preferably coloring agents.

The preservatives can be the conventional preservatives in the field. The antioxidants can be the conventional antioxidants in the field. The color fixatives can be the conventional color fixatives in the field. The bleaches can be the conventional bleaches in the field. The acidulants can be the conventional acidulants in the field. The coagulants can be the conventional coagulants in the field. The bulking agents can be the conventional bulking agents in the field. The thickeners can be the conventional thickeners in the field. The defoaming agents can be the conventional defoaming agents in the field. The sweetening agents can be the conventional sweetening agents in the field. The emulsifiers can be the conventional emulsifiers in the field. The quality modifiers can be the conventional quality modifiers in the field. The anti-caking agents can be the conventional anti-caking agents in the field. The palatability enhancers can be the conventional palatability enhancers in the field. The enzyme preparations can be the conventional enzyme preparations in the field. The coating agents can be the conventional coating agents in the field. The foaming agents can be the conventional foaming agents in the field. The antistaling agents can be the conventional antistaling agents in the field. The flavours can be the conventional flavours in the field. The nutrition enhancers can be the conventional nutrition enhancers in the field. The coloring agents can be the conventional coloring agents in the field, preferably amaranth, carmine, red (etythrosine), new red, allura red, lemon yellow, sunset yellow, brilliant blue, indigo and their respective aluminum lake, preferably titanium aluminium lake.

The amount of the food additives can be the conventional dosage in the field. There are no special restrictions in the present invention. According to the requirements of prescription process to adjust the dosage. The amount of the food additives preferably from 0 to 1 and not to be 0.

In the present invention, the salt in "pharmaceutically acceptable salt" can be in the form of the conventional salt in the field, preferably including but not limited to wherein inorganic salt including hydrochloride, sulfate, phosphate, nitrate, hydrobromide, hydroiodate, and hydrogen sulfate; organic acid salt including triflate, p-toluenesulfonate, 1-naphthalene sulfonate, trifluoroacetate, malate, fumarate, benzoate, salicylate, phenylacetate, acetate, adipate, alginate, ascorbate, aspartate acid salt, benzoate, benzene sulfonate, butyrate, citrate, camphorate, camphor sulfonate, cinnamate, cyclopentylpropionate, bis-gluconate, lauryl sulfate, isethionate, fumarate, glucoheptanoate, glycerophosphate, hemisulfate, heptanoate, 2-hydroxyethyl sulfonate, itaconate, lactate, maleate acid salt, mandelate, methanesulfonate, 2-naphthalenesulfonate, nicotinate, oxalate, pamoate, pectinate, persulfate, 3-phenylpropionate, picrate, trimethylacetate, propionate, succinate, sulfonate, tartarate, thiocyanate, or tosylate.

In some preferred embodiments of the present invention, the pharmaceutical composition comprises the following components. The components can be any of the followings, involving amount is measured by weight:

Or, the active pharmaceutical ingredients are present in an amount from 0.5 to 15, the diluents are present in an amount from 10 to 98 and the lubricants are present in an amount from 0.1 to 5;

Or, the active pharmaceutical ingredients are present in an amount from 0.5 to 15, the diluents are present in an amount from 59 to 98 and the lubricants are present in an amount from 0.5 to 3;

Or, the active pharmaceutical ingredients are present in an amount from 0.5 to 15, the diluents are present in an amount from 80 to 98 and the lubricants are present in an amount from 0.5 to 3;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount from 0.5 to 15, microcrystalline cellulose PH102 is present in an amount from 80 to 98 and magnesium stearate is present in an amount from 0.5 to 3;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount of 3.3, microcrystalline cellulose PH102 is present in an amount of 95.7 and magnesium stearate is present in an amount of 1;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount of 13.3, microcrystalline cellulose PH102 is present in an amount of 85.7 and magnesium stearate is present in an amount of 1;

Or, active pharmaceutical ingredients, diluents, disintegrants and lubricants.

Or, the active pharmaceutical ingredients are present in an amount from 0.5 to 15, the diluents are present in an amount from 10 to 98, the disintegrants are present in an amount from 0.5 to 20 and the lubricants are present in an amount from 0.1 to 5;

Or, the active pharmaceutical ingredients are present in an amount from 0.5 to 15, the diluents are present in an amount from 59 to 98, the disintegrants are present in an amount from 0.5 to 10 and the lubricants are present in an amount from 0.5 to 3;

Or, the active pharmaceutical ingredients are present in an amount from 0.5 to 15, the diluents are present in an amount from 80 to 98, the disintegrants are present in an amount from 0.5 to 3 and the lubricants are present in an amount from 0.5 to 3;

Or, 3-((1H-pyrazolo[3,4-b]pyridin-5-yl)ethynyl)-4-methyl-N-(4-((4-methylpiperazin-1-y)methyl)-3-(trifluoromethyl)phenyl)-benzamide is present in an amount from 0.5 to 15, microcrystalline cellulose PH102 is present in an amount from 80 to 98, croscarmellose sodium is present in an amount from 0.5 to 3 and magnesium stearate is present in an amount from 0.5 to 3;

Or, 3-((1H-pyrazolo[3,4-b]pyridin-5-yl)ethynyl)-4-methyl-N-(4-((4-methylpiperazin-1-y)methyl)-3-(trifluoromethyl)phenyl)-benzamide is present in an amount of 14.29, microcrystalline cellulose PH102 is present in an amount of 84.21, croscarmellose sodium is present in an amount of 1 and magnesium stearate is present in an amount of 0.5;

Or, active pharmaceutical ingredients, diluents, disintegrants, lubricants and food additives;

Or, active pharmaceutical ingredients are present in an amount from 0.5 to 15, diluents are present in an amount from 10 to 98, disintegrants are present in an amount from 0.5 to 20, lubricants are present in an amount from 0.1 to 5 and food additives are present in an amount from 0 to 1;

Or, active pharmaceutical ingredients are present in an amount from 0.5 to 15, diluents are present in an amount from 59 to 98, disintegrants are present in an amount from 0.5 to 10, lubricants are present in an amount from 0.5 to 3 and food additives are present in an amount from 0 to 1;

Or, active pharmaceutical ingredients are present in an amount from 0.5 to 15, diluents are present in an amount from 80 to 98, disintegrants are present in an amount from 0.5 to 3, lubricants are present in an amount from 0.5 to 3 and food additives are present in an amount from 0 to 1;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount from 0.5 to 15, microcrystalline cellulose PH102 is present in an amount from 80 to 98, croscarmellose sodium is present in an amount from 0.5 to 3, magnesium stearate is present in an amount from 0.5 to 3 and titanium aluminium lake is present in an amount from 0 to 1;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount of 1.43, microcrystalline cellulose PH102 is present in an amount of 96.67, croscarmellose sodium is present in an amount of 1, magnesium stearate is present in an amount of 0.5 and titanium aluminium lake is present in an amount of 0.4;

Active pharmaceutical ingredients, diluents, disintegrants, lubricants and food additives are the same as described above.

In some preferred embodiments of the present invention, the pharmaceutical composition can be present in the form of solid preparations, preferably tablets, dispersants, granules or capsules, more preferably tablets or capsules.

In some preferred embodiments of the present invention, when the pharmaceutical composition is in the form of a tablet, the pharmaceutical composition comprises the following components. The components can be any of the followings, involving amount is measured by weight:

Or, active pharmaceutical ingredients, diluents, disintegrants and lubricants.

Or, the active pharmaceutical ingredients are present in an amount from 0.5 to 15, the diluents are present in an amount from 10 to 98, the disintegrants are present in an amount from 0.5 to 20 and the lubricants are present in an amount from 0.1 to 5;

Or, the active pharmaceutical ingredients are present in an amount from 0.5 to 15, the diluents are present in an amount from 59 to 98, the disintegrants are present in an amount from 0.5 to 10 and the lubricants are present in an amount from 0.5 to 3;

Or, the active pharmaceutical ingredients are present in an amount from 0.5 to 15, the diluents are present in an amount from 80 to 98, the disintegrants are present in an amount from 0.5 to 3 and the lubricants are present in an amount from 0.5 to 3;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount from 0.5 to 15, microcrystalline cellulose PH102 is present in an amount from 80 to 98, croscarmellose sodium is present in an amount from 0.5 to 3 and magnesium stearate is present in an amount from 0.5 to 3;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount of 14.29, microcrystalline cellulose PH102 is present in an amount of 84.21, croscarmellose sodium is present in an amount of 1 and magnesium stearate is present in an amount of 0.5;

Or, active pharmaceutical ingredients, diluents, disintegrants, lubricants and food additives;

Or, active pharmaceutical ingredients are present in an amount from 0.5 to 15, diluents are present in an amount from 10 to 98, disintegrants are present in an amount from 0.5 to 20, lubricants are present in an amount from 0.1 to 5 and food additives are present in an amount from 0 to 1;

Or, active pharmaceutical ingredients are present in an amount from 0.5 to 15, diluents are present in an amount from 59 to 98, disintegrants are present in an amount from 0.5 to 10, lubricants are present in an amount from 0.5 to 3 and food additives are present in an amount from 0 to 1;

Or, active pharmaceutical ingredients are present in an amount from 0.5 to 15, diluents are present in an amount from 80 to 98, disintegrants are present in an amount from 0.5 to 3, lubricants are present in an amount from 0.5 to 3 and food additives are present in an amount from 0 to 1;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount from 0.5 to 15, microcrystalline cellulose PH102 is present in an amount from 80 to 98, croscarmellose sodium is present in an amount from 0.5 to 3, magnesium stearate is present in an amount from 0.5 to 3 and titanium aluminium lake is present in an amount from 0 to 1;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount of 1.43, microcrystalline cellulose PH102 is present in an amount of 96.67, croscarmellose sodium is present in an amount of 1, magnesium stearate is present in an amount of 0.5 and titanium aluminium lake is present in an amount of 0.4;

Active pharmaceutical ingredients, diluents, disintegrants, lubricants and food additives are the same as described above.

In some preferred embodiments of the present invention, when the pharmaceutical composition is in the form of tablet, the tablet can include tablet core. The tablet core comprises the pharmaceutical composition which is the same as described above. Tablets can mask unpleasant tastes or extend the disintegration and absorption in the gastrointestinal tract by not coating or by known coating techniques, providing a longer duration of drug efficacy. Therein, the coating is carried out under the condition of adding the conventional coating medium and film forming agent in the field (they are generally referred to as coating materials). The coating material is preferably one or more of the hydroxypropyl cellulose, hydroxypropyl methyl cellulose, ethyl cellulose, polyvinylpyrrolidone and vinylpyrrolidone-vinyl acetate copolymer. The coating is preferably a film coat (for example, a gastro-soluble film coat or an enteric-coated film coat) or a sugar coating, preferably a film coat, and further preferably a gastro-soluble film coat. The coating is preferably accounts for from 2% to 5% of the tablet core weight, more preferably from 2.5% to 4%, and further preferably from 2.5% to 3.5%.

In some preferred embodiments of the present invention, when the pharmaceutical composition is in the form of a tablet, the specification of the tablet can be the conventional specification in the field. In terms of active pharmaceutical ingredients, the specification of the tablet is preferably from 1 mg/tablet to 100 mg/tablet, more preferably 1 mg/tablet, 2 mg/tablet, 5 mg/tablet, 10 mg/tablet, 20 mg/tablet, 30 mg/tablet, 40 mg/tablet, 50 mg/tablet or 60 mg/tablet, further preferably 1 mg/tablet, 10 mg/tablet, 20 mg/tablet, 30 mg/tablet or 40 mg/tablet.

In some preferred embodiments of the present invention, when the pharmaceutical composition is in the form of a capsule, the pharmaceutical composition includes the following components. The components can be in any of the followings. The amount involved is measured by weight:

Or, the active pharmaceutical ingredients are present in an amount from 0.5 to 15, the diluents are present in an amount from 10 to 98 and the lubricants are present in an amount from 0.1 to 5;

Or, the active pharmaceutical ingredients are present in an amount from 0.5 to 15, the diluents are present in an amount from 59 to 98 and the lubricants are present in an amount from 0.5 to 3;

Or, the active pharmaceutical ingredients are present in an amount from 0.5 to 15, the diluents are present in an amount from 80 to 98 and the lubricants are present in an amount from 0.5 to 3;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount from 0.5 to 15, microcrystalline cellulose PH102 is present in an amount from 80 to 98 and magnesium stearate is present in an amount from 0.5 to 3;

Or, 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide is present in an amount of 3.3, microcrystalline cellulose PH102 is present in an amount of 95.7 and magnesium stearate is present in an amount of 1;

The active pharmaceutical ingredients, diluents and lubricants are the same as described above.

In some preferred embodiments of the present invention, when the pharmaceutical composition is in the form of capsules, the specification of the capsules can be the conventional specification in the field, for example: 1 mg/grain, 10 mg/grain, 20 mg/grain, 30 mg/grain, 40 mg/grain, preferably 10 mg/grain, 20 mg/grain.

The present invention provides a preparation method for the pharmaceutical composition mentioned above, which includes the following steps: mixing the components together.

The present invention provides a preparation method of the pharmaceutical composition, which can be method 1 or method 2 when the pharmaceutical composition is in the form of tablets.

The method I consists of the following steps:
A1: Sieve the active pharmaceutical ingredients and available pharmaceutical excipients respectively;
A2: Sieve the active pharmaceutical ingredients and part of the diluents to get the mixture;
A3: Add the remaining diluents into the mixture of Step A2 and sieve to get the mixture;
A4: Pellet the mixture of step A3 to get particles;
A5: Sieve and pelletize the particles of Step A4 and lubricants;
A6: Press and pack;

The method II consists of the following steps:
B1: Sieve the active pharmaceutical ingredients, diluents and disintegrating agents, the internal added lubricants and external added lubricants;

B2: Mix the active pharmaceutical ingredients and diluents to get premix 1, sieve premix 1, sieve disintegrants and remaining diluents to wash the machine, and mix with the screened premix 1, Sieve the mixture twice again to get premix 2;
B3: Mix premix 2 with internal added lubricant to get premix 3;
B4: Pellet premix 3 to get particles, mix the particles with external added lubricant to get premix 4;
B5: Press premix 4 and then pack; Or pellet premix 4, and then press and pack.

In some preferred embodiment of the present invention, in step A1, the active pharmaceutical ingredients are preferably to sieve with 200 meshes. The available pharmaceutical excipients for sieving are preferably from 40 meshes to 100 meshes.

In some preferred embodiments of the present invention, in step A2, the sieving is preferably with 40 meshes. The times of the sieving are preferably from 5 to 15 times (for example, 10 times).

In some preferred embodiments of the present invention, in step A2, food additives and/or disintegrating agents are preferably added to sieve together.

In some preferred embodiments of the present invention, in step A3, the sieving is preferably with 40 meshes. The times of the sieving are preferably from 5 to 15 times (for example, 10 times).

In some preferred embodiments of the present invention, in step A4, the method of pelleting is preferably to use dry granulation.

In some preferred embodiments of the present invention, in step A5, the sieving is preferably with 24 meshes. The times of the sieving are preferably from 5 to 15 times (for example, 10 times). The method of pelleting is preferably to use dry granulation.

In some preferred embodiments of the present invention, in step A5, the disintegrating agents are preferably added to sieve together.

In some preferred embodiments of the present invention, in step A6, the method of pressing is preferably to use Φ5.0 mm flat concave die. The method of pressing is preferably with hardness from 30N to 70N.

In some preferred embodiments of the present invention, in step B1, the active pharmaceutical ingredients are preferably to use ball mill or microgrinder to smash, more preferably microgrinder.

In some preferred embodiments of the present invention, in step B1, the active pharmaceutical ingredients, diluents and disintegrating agents are preferably to use 20 meshes to sieve.

In some preferred embodiments of The present invention, in step B1, the inners and outer lubricants are preferably to use 60 meshes to sieve.

In some preferred embodiments of the present invention, in step B2, the active pharmaceutical ingredients mix with the diluents, the diluents are preferably to use 2 times of the active pharmaceutical ingredients.

In some preferred embodiments of the present invention, in step B2, the active pharmaceutical ingredients mix with the diluents, and the mixing is preferably in a barrel mixer.

In some preferred embodiments of the present invention, in step B2, the sieving is preferably to use Comil.

In some preferred embodiments of the present invention, in step B3, mix premix 2 with internal added lubricant, the mixing is preferably in a mixing drum.

In some preferred embodiments of the present invention, in step B4, Pellet premix 3 to get particles, the pelleting is preferably in a roller pelleting machine. The pelleting is preferably to use dry granulation.

In some preferred embodiments of the present invention, in step B4, mix the particles with external added lubricant, and the mixing is preferably in a barrel mixer.

In some preferred embodiments of the present invention, in step B4, take samples to detect the mixing uniformity, LOD, particle size distribution, etc. after the end of mixing.

The present invention provides a preparation method of the pharmaceutical composition, when the pharmaceutical composition is in the form of a capsule, the method comprises the following steps:

C1: Sieve the active pharmaceutical ingredients and available pharmaceutical excipients respectively;

C2: Sieve the active pharmaceutical ingredients and part of the diluents to get the mixture;

C3: Add the remaining diluents into the mixture of step C2 in several times, then sieve to get the mixture;

C4: Sieve the mixture of C3 and lubricants to get the mixture;

C5: Fill the C4 mixture into the capsule and pack.

In some preferred embodiments of the present invention, in step C1, the active pharmaceutical ingredients are preferably to use 40 meshes to sieve.

In some preferred embodiments of the present invention, in step C2, is preferably to use 40 meshes to sieve. The times of the sieving are preferably from 5 to 15 times (for example, 10 times).

In some preferred embodiments of the present invention, in step C3, is preferably to use 40 meshes to sieve. The times of the sieving are preferably from 5 to 15 times (for example, 10 times).

In some preferred embodiments of the present invention, in step C4, is preferably to use 40 meshes to sieve. The times of the sieving are preferably from 5 to 15 times (for example, 10 times).

The present invention also provides an application of the above-mentioned pharmaceutical composition in preparation of pharmaceuticals. The pharmaceuticals are preferably a pharmaceutical for the prevention and/or treatment of tumors. The tumors are preferably one or more of leukemia, gastrointestinal stromal tumors, histiocytic lymphoma, non-small cell lung cancer, small cell lung cancer, lung adenocarcinoma, lung squamous cell carcinoma, pancreatic cancer, breast cancer, prostate cancer, liver cancer, skin cancer, epithelial cell cancer, prostate cancer, and nasopharyngeal cancer.

The present invention also provides a method for preventing and/or treating of tumors, includes providing an administration to patient of therapeutic effective amount of the above-mentioned pharmaceutical composition. The tumors are preferably one or more of leukemia, gastrointestinal stromal tumors, histiocytic lymphoma, non-small cell lung cancer, small cell lung cancer, lung adenocarcinoma, lung squamous cell carcinoma, pancreatic cancer, breast cancer, prostate cancer, liver cancer, skin cancer, epithelial cell cancer, prostate cancer, and nasopharyngeal cancer.

In the present invention, the open writing "including" can be converted into a closed writing "consists of".

The present invention achieves beneficial effects of:

1, The present invention provides a pharmaceutical composition of 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide for the first time, especially a prescription preparation can be used in clinical treatment, the preparation has significant technical advantage on the product stability, mobility and bioavailability.

2, The present invention makes rigorous and scientific sieve for the types of excipients and ratios of above-mentioned pharmaceutical compositions, and effectively improves quality standard of the tablets.

3, In the process of screening of formulation and technology, when the tablet specification is small, the loose density and fluidity of each component are not the same that the content uniformity of the tablet will be affected by direct compression. The method of adding raw and auxiliary materials by equal amount and the dry granulation process are used to achieve better content uniformity of the tablets.

4, The tablet technology of the present invention was prepared by dry process preparation which can effectively increases the stability of the tablet, can make production process simple, varieties of excipients use less, operation simple and smooth, reproducibility good, product quality good. There are no special requirements for the packaging and storage conditions of the preparation to make it suitable for industrial production.

EMBODIMENTS FOR CARRYING OUT THE INVENTION

In order to simplify statements, the compound referred to in the following embodiments means 3-((1H-pyrazolo[3,4-b]pyridin-5-yl)ethynyl)-4-methyl-N-(4-((4-methylpiperazin-1-yl)methyl)-3-(trifluoromethyl)phenyl)-benzamide.

Embodiment 1: Compound Tablets

Formulation Composition:

| Component | Amount | Weight percentage (%) |
| --- | --- | --- |
| Compound | 9.5 g | 1.43 |
| Tartrazine aluminium lake | 2.66 g | 0.40 |
| Microcrystalline cellulose PH102 | 642.9 g | 96.67 |
| Croscarmellose sodium | 6.65 g | 1.00 |
| Magnesium stearate | 3.325 g | 0.50 |
| Complete production | 665.035 g | 100.0 |

The preparation method Comprises:

Step 1: sieve the compound with 200 meshes, the tartrazine aluminium lake with 100 meshes, the microcrystalline cellulose PH102, the croscarmellose sodium and the magnesium stearate with 40 meshes;

Step 2: sieve the compound, 5/100 microcrystalline cellulose PH102, tartrazine aluminium lake and 1/4 croscarmellose sodium with 40 meshes, sieve 10 times to get mixture (I);

Step 3: take out about 7/100 microcrystalline cellulose PH102 to add the powder mixture of the previous step, sieve with 40 meshes, sieve 10 times to get mixture (II);

Step 4: take out about 16/100 microcrystalline cellulose PH102 to add the powder mixture of the previous step, sieve with 40 meshes, sieve 10 times to get mixture (III);

Step 5: take out about 30/100 microcrystalline cellulose PH102 to add the powder mixture of the previous step, sieve with 40 meshes, sieve 10 times to get mixture (IV);

Step 6: take out about 42/100 microcrystalline cellulose PH102 to add the powder mixture of the previous step, sieve with 40 meshes, sieve 10 times to get mixture (V);

Step 7: take out pre-mixed powder for dry granulation;

Step 8: take out the granules from dry type granulator to add 3/4 croscarmellose sodium and magnesium stearate, sieve with 24 meshes for 10 times to mix together. After mixing together, make a second dry granulation to detect the content and uniformity of intermediates;

Step 9: Φ5.0 mm flat concave die was used for tabletting, 30-70N in hardness;

Step 10: Package.

Embodiment 2: Compound Tablets

Formulation Composition:

| Component | Amount | Weight percentage (%) |
|---|---|---|
| Compound | 15 g | 1.43 |
| Tartrazine aluminium lake | 4.20 g | 0.40 |
| Microcrystalline cellulose PH102 | 1015 g | 96.67 |
| Croscarmellose sodium | 10.50 g | 1.00 |
| Magnesium stearate | 5.25 g | 0.50 |
| Complete production | 1049.95 g | 100.0 |

The preparation method as described in embodiment 1.

Embodiment 3: Compound Tablets

Formulation Composition:

| Component | Amount | Weight percentage (%) |
|---|---|---|
| Compound | 106 g | 14.29 |
| Microcrystalline cellulose PH102 | 624.9 g | 84.21 |
| Croscarmellose sodium | 7.42 g | 1.00 |
| Magnesium stearate | 3.71 g | 0.50 |
| Complete production | 742.03 g | 100.0 |

The preparation method comprises:

Step 1: sieve the compound with 200 meshes, the microcrystalline cellulose PH102, the croscarmellose sodium and the magnesium stearate with 40 meshes;

Step 2: sieve the compound, 16/100 microcrystalline cellulose PH102 and 1/4 croscarmellose sodium with 40 meshes, sieve 10 times to get mixture (I);

Step 3: take out about 34/100 microcrystalline cellulose PH102 to add the powder mixture of the previous step, sieve with 40 meshes, sieve 10 times to get mixture (II);

Step 4: take out about 50/100 microcrystalline cellulose PH102 to add the powder mixture of the previous step, sieve with 40 meshes, sieve 10 times to get mixture (III);

Step 5: take out pre-mixed powder for dry granulation;

Step 6: take out the granules from dry type granulator to add 3/4 croscarmellose sodium and magnesium stearate, sieve with 24 meshes for 10 times to mix together. After mixing together, make a second dry granulation to detect the content and uniformity of intermediates;

Step 7: Φ5.0 mm flat concave die was used for tabletting, 30-70N in hardness;

Step 8: Package.

Embodiment 4: Compound Tablets

Formulation Composition:

| Component | Amount | Weight percentage (%) |
|---|---|---|
| Compound | 4.00 Kg | 14.29 |
| Microcrystalline cellulose PH102 | 23.56 Kg | 84.21 |
| Croscarmellose sodium | 0.28 Kg | 1.00 |
| Magnesium stearate | 0.14 Kg | 0.50 |
| Complete production | 28.00 Kg | 100.0 |

The preparation method comprises:

Step 1: sieve the compound, the microcrystalline cellulose PH102 and the croscarmellose sodium with 20 meshes, sieve the internal added lubricants and external added lubricants with 60 meshes;

Step 2: mix the compound and twice amount as the compound as microcrystalline cellulose in barrel mixer to get premix 1;

Step 3: sieve premix 1 with Comil, sieve all croscarmellose sodium and remaining microcrystalline cellulose with Comil to wash the machine, and mix with the screened premix 1, sieve the mixture twice again to get premix 2;

Step 4: lubricate before roller compression and granulation: lubricate the premix 2 and 50% prescription amount of magnesium stearate into mixing drum;

Step 5: take out pre-mixed premix into rolling granulator for dry granulation;

Step 6: take out the granules from bucket type of blender to lubricate together with 50% prescription amount of magnesium stearate, to detect the mixing uniformity, LOD and particle size distribution of samples;

Step 7: press and package.

Embodiment 5: Compound Capsules

Formulation Composition:

| Component | | Amount | Weight percentage (%) |
|---|---|---|---|
| Contents | Compound | 5 g | 3.3 |
| | Microcrystalline cellulose PH102 | 143.5 g | 95.7 |
| | Magnesium stearate | 15 g | 1.00 |
| 3# gelatin empty capsule | | 1000 grain | N/A |
| Complete production | | 1000 grain | 100.0 |

N/A means no result was detected.

The preparation method comprises:

Step 1: sieve the compound, microcrystalline cellulose PH102 and magnesium stearate with 40 meshes;

Step 2: take out the compound, 14/100 microcrystalline cellulose PH102 with 40 mesh sieve, sieve 10 times to get mixture (I);

Step 3: take out about 28/100 microcrystalline cellulose PH102 to add the powder mixture of the previous step, sieve with 40 meshes, sieve 10 times to get mixture (II);

Step 4: take out about 58/100 microcrystalline cellulose PH102 to add the powder mixture of the previous step, sieve with 40 meshes, sieve 10 times to get mixture (III);

Step 5: sieve the mixture (III) and prescriptions of magnesium stearate with 40 meshes, sieve 10 times to get total mixed powders, to detect the content and uniformity of intermediates;

Step 6: take out the total mixed powders, fill them into 3# gelatin empty capsule, control the loading amount to 150 mg±7.5%;

Step 7: package.

Embodiment 6: Compound Capsules

Formulation Composition:

|  | Component | Amount | Weight percentage (%) |
|---|---|---|---|
| Contents | Compound | 20 g | 13.3 |
|  | Microcrystalline cellulose PH102 | 128.5 g | 85.7 |
|  | Magnesium stearate | 15 g | 1.00 |
| 3# gelatin empty capsule |  | 1000 grain | N/A |
| Complete production |  | 1000 Grain | 100.0 |

N/A means no result was detected.

The preparation method as described in embodiment 5.

Embodiment 6

Detect powder characteristic, mixing uniformity, tablet weight difference, fragility, disintegration time limit and tablet dissolution of mixed powder of above embodiments. Results are as follows:

| Test items | Embodiment 1 | Embodiment 2 | Embodiment 3 | Embodiment 4 | Embodiment 5 | Embodiment 6 |
|---|---|---|---|---|---|---|
| Apparent density (g/ml) | 0.538 | 0.563 | 0.574 | 0.573 | 0.444 | 0.446 |
| Carl index (%) | 24.9 | 24.1 | 25.2 | 27.5 | 20.1 | 20.1 |
| Mixing uniformity (RSD %, n = 10) | 0.5 | 1.8 | 0.4 | 0.5 | N/A | N/A |
| Dissolution rate (%) | N/A | N/A | 97 | 96 | N/A | N/A |
| Weight/load difference | Qualified | Qualified | Qualified | Qualified | Qualified | Qualified |
| Tablet Friability (%) | Qualified | Qualified | Qualified | Qualified | N/A | N/A |
| Disintegration time | 7 seconds | 2 minutes 20 seconds | N/A | 20 seconds | N/A | N/A |

N/A means no result was detected.

In embodiments 1-6, the compound of embodiments 4 was preprocessed with 20 meshes. The mixing process uses hopper mixing machine and Comil granulate machine. The process can be used for amplification production, and central control indexes (mixing uniformity, dissolution, weight/load difference, Friability and disintegration time) all meet the preparation standards, which is better than other embodiments.

Although the above describes the specific embodiments of the present invention, technicians in the field should understand that these are only examples. Variety of variations or modifications can be made to these embodiments without deviating from the principles and essence of the present invention. Therefore, the scope of protection of the present invention is limited by the attached claims.

We claim:

1. A pharmaceutical composition, comprising an active pharmaceutical ingredient and available pharmaceutical excipients; wherein the active pharmaceutical ingredient is 3-((1H-pyrazolo[3,4-b]pyridin-5-yl)ethynyl)-4-methyl-N-(4-((4-methylpiperazin-l-yl)methyl) -3-(trifluoromethyl) phenyl)-benzamide in an amount from 0.5% to 15% by weight, or a pharmaceutically acceptable salt thereof;
wherein the available pharmaceutical excipients include diluents selected from one or more of calcium hydrogen phosphate, kaolin, dextrin, lactose, sucrose, microcrystalline cellulose, powdered cellulose, calcium carbonate, sorbitol powder, starch, starch derivatives, erythritol, xylitol, and fructose, and lubricants selected from one or more of magnesium stearate, stearic acid, calcium stearate, zinc stearate, liquid paraffin wax, polyethylene glycol, silica, colloidal silica, siliciidoxydum, talcum powder, starch, and hydrogenated vegetable oil.

2. The pharmaceutical composition according to claim 1, wherein
the amount of the pharmaceutical active ingredient is from 1% to 14.5% by weight;
the diluents is selected from dextrin, lactose, microcrystalline cellulose and starch and the amount of the diluent is from 10% to 98%, from 20% to 98%, from 59% to 98%, or from 80% to 98%, by weight;
the lubricant is selected from magnesium stearate, stearic acid, calcium stearate and siliciidoxydum
and the amount of the lubricant is from 0.1% to 5%, or from 0.5% to 3% by weight.

3. The pharmaceutical composition according to claim 2, wherein the diluent is microcrystalline cellulose PH102 or starch derivatives selected from one or more of corn starch, potato starch, compressible starch, modified starch, and pregelatinized starch.

4. The pharmaceutical composition according to claim 2, wherein the available pharmaceutical excipients further include disintegrating agents, wherein the disintegrating agent is selected from one or more of low-substituted hydroxypropyl cellulose, crosslinked polyvingypyrrolidone, crosslinked carboxymethyl starch sodium, sodium carboxymethyl starch, and croscarmellose sodium, carboxymethyl wherein the amount of the disintegrating agents is from 0.5% to 20%, from 0.5% to 10%, or from 0.5% to 3% by weight.

5. The pharmaceutical composition according to claim 2, wherein the available pharmaceutical excipients further include adhesives selected from one or more of hydroxypropyl cellulose, hydroxypropyl methyl cellulose, polyvinylpyrrolidone, polyvinyl alcohol, arabic gum, alginic acid, sodium alginate, and gelatin, wherein the amount of the adhesives is from 0.1% to 5%, or from 0.5% to 3% by weight.

6. The pharmaceutical composition according to claim 2, wherein the available pharmaceutical excipients further include wetting agents, wherein the wetting agent is selected from one or more of polysorbates, polyoxyethylene aliphatic alcohol ethers, polyoxyethylene castor oils, phospholipids, hydrosulfates, poloxamer, or sodium lauryl sulfate;

wherein the amount of the wetting agents is greater than 0% and less than 10% or from 0.1% to 10% by weight.

7. The pharmaceutical composition according to claim 2, further comprising food additives, wherein the food additive is selected from one or more of preservatives, antioxidants, color fixatives, bleaches, acidulants, coagulants, bulking agents, thickeners, defoaming agents, sweetening agents, coloring agents, emulsifiers, quality modifiers, anti-caking agents, palatability enhancers, enzyme preparations, coating agents, foaming agents, preservatives, flavours, and nutrition enhancers, wherein the amount of the food additives is greater than 0% and less than 10% by weight.

8. The pharmaceutical composition according to claim 2, wherein the pharmaceutical composition comprises the active pharmaceutical ingredients, diluents, disintegrants, lubricants, and optionally food additives; all of which is measured by weight, wherein:
the active pharmaceutical ingredient is present in an amount from 1% to 14.5%, the diluents are present in an amount from 10% to 98%, and the lubricants are present in an amount from 0.1% to 5%;
or, the active pharmaceutical ingredient is present in an amount from 1% to 14.5%, the diluents are present in an amount from 59% to 98%, and the lubricants are present in an amount from 0.5% to 3%;
or, the active pharmaceutical ingredient is present in an amount from 1% to 14.5%, the diluents are present in an amount from 80% to 98%, and the lubricants are present in an amount from 0.5% to 3%;
or, the active pharmaceutical ingredient is present in an amount from 1% to 14.5%, microcrystalline cellulose PH102 is present in an amount from 80% to 98%, and magnesium stearate is present in an amount from 0.5% to 3%;
or, the active pharmaceutical ingredient is present in an amount of 3.3%, microcrystalline cellulose PH102 is present in an amount of 95.7%, and magnesium stearate is present in an amount of 1%;
or, the active pharmaceutical ingredient is present in an amount of 13.3%, microcrystalline cellulose PH102 is present in an amount of 85.7%, and magnesium stearate is present in an amount of 1%;
or, the active pharmaceutical ingredient is present in an amount from 1% to 14.5%, the diluents are present in an amount from 10% to 98%, the disintegrants are present in an amount from 0.5% to 20%, and the lubricants are present in an amount from 0.1% to 5%;
or, the active pharmaceutical ingredient is present in an amount from 1% to 14.5%, the diluents are present in an amount from 20% to 98%, the disintegrants are present in an amount from 0.5% to 10%, and the lubricants are present in an amount from 0.5% to 3%;
or, the active pharmaceutical ingredient present in an amount from 1% to 14.5%, the diluents are present in an amount from 80% to 98%, the disintegrants are present in an amount from 0.5% to 3%, and the lubricants are present in an amount from 0.5% to 3%;
or, the active pharmaceutical ingredient is present in an amount from 1% to 14.5%, microcrystalline cellulose PH102 is present in an amount from 80% to 98%, croscarmellose sodium is present in an amount from 0.5% to 3%, and magnesium stearate is present in an amount from 0.5% to 3%;
or, the active pharmaceutical ingredient is present in an amount of 14.29%, microcrystalline cellulose PH102 is present in an amount of 84.21%, croscarmellose sodium is present in an amount of 1%, and magnesium stearate is present in an amount of 0.5%;
or, the active pharmaceutical ingredient is present in an amount from 1% to 14.5%, diluents are present in an amount from 10% to 98%, disintegrants are present in an amount from 0.5% to 20%, lubricants are present in an amount from 0.1% to 5%, and food additives are present in an amount from 0% to 1%;
or, the active pharmaceutical ingredient is present in an amount from 1% to 14.5%, diluents are present in an amount from 59% to 98%, disintegrants are present in an amount from 0.5% to 10%, lubricants are present in an amount from 0.1 to 3, and food additives are present in an amount from 0% to 1%;
or, the active pharmaceutical ingredient is present in an amount from 1% to 14.5%, diluents are present in an amount from 80% to 98%, disintegrants are present in an amount from 0.5% to 3%, lubricants are present in an amount from 0.5% to 3%, and food additives are present in an amount from 0% to 1%;
or, the active pharmaceutical ingredient is present in an amount from 1% to 14.5%, microcrystalline cellulose PH102 is present in an amount from 80% to 98%, croscarmellose sodium is present in an amount from 0.5% to 3%, magnesium stearate is present in an amount from 0.5% to 3%, and titanium aluminium lake is present in an amount from 0% to 1%;
or, the active pharmaceutical ingredient is present in an amount of 1.43%, microcrystalline cellulose PH102 is present in an amount of 96.67%, croscarmellose sodium is present in an amount of 1, magnesium stearate is present in an amount of 0.5%, and titanium aluminium lake is present in an amount of 0%.

9. The pharmaceutical composition according to claim 2, wherein the pharmaceutical composition is in the form of solid preparations selected from, tablets, dispersants, granules, or capsules.

10. The pharmaceutical composition according to claim 9, wherein the tablet comprises the active pharmaceutical ingredient, diluents, disintegrants, lubricant, and optionally food additives, all of which is measured by weight, wherein:
the active pharmaceutical ingredient is present in an amount from 1% to 14.5%, the diluents are present in an amount from 10% to 98%, the disintegrants are present in an amount from 0.5% to 20%, and the lubricants are present in an amount from 0.1% to 5%;
or, the active pharmaceutical ingredient is present in an amount from 1% to 14.5%, the diluents are present in an amount from 59% to 98%, the disintegrants are present in an amount from 0.5% to 10%, and the lubricants are present in an amount from 0.5% to 3%;
or, the active pharmaceutical ingredient is present in an amount from 1% to 14.5%, the diluents are present in an amount from 80% to 98%, the disintegrants are present in an amount from 0.5% to 3%, and the lubricants are present in an amount from 0.5% to 3%;
or, the active pharmaceutical ingredient is present in an amount from 1% to 14.5%, microcrystalline cellulose PH102 is present in an amount from 80% to 98%, croscarmellose sodium is present in an amount from 0.5% to 3%, and magnesium stearate is present in an amount from 0.5% to 3%;
or, the active pharmaceutical ingredient is present in an amount of 14.29%, microcrystalline cellulose PH102 is present in an amount of 84.21%, croscarmellose sodium is present in an amount of 1%, and magnesium stearate is present in an amount of 0.5%;

or, the active pharmaceutical ingredient is present in an amount from 1% to 14.5%, diluents are present in an amount from 10% to 98%, disintegrants are present in an amount from 0.5% to 20%, lubricants are present in an amount from 0.1% to 5%, and food additives are present in an amount from 0% to 1%;

or, the active pharmaceutical ingredient is present in an amount from 1% to 14.5%, diluents are present in an amount from 59% to 98%, disintegrants are present in an amount from 0.5% to 10%, lubricants are present in an amount from 0.1% to 3%, and food additives are present in an amount from 0% to 1%;

or, the active pharmaceutical ingredient is present in an amount from 1% to 14.5%, diluents are present in an amount from 80% to 98%, disintegrants are present in an amount from 0.5% to 3%, lubricants are present in an amount from 0.5% to 3%, and food additives are present in an amount from 0% to 1%;

or the active pharmaceutical ingredient is present in an amount from 1% to 14.5%, microcrystalline cellulose PH102 is present in an amount from 80% to 98%, croscarmellose sodium is present in an amount from 0.5% to 3%, magnesium stearate is present in an amount from 0.5% to 3%, and titanium aluminium lake is present in an amount from 0% to 1%;

or, the active pharmaceutical ingredient is present in an amount of 1.43%, microcrystalline cellulose PH102 is present in an amount of 96.67%, croscarmellose sodium is present in an amount of 1%, magnesium stearate is present in an amount of 0.5%, and titanium aluminium lake is present in an amount of 0%.

11. The pharmaceutical composition according to claim 10, wherein when the pharmaceutical composition is in the form of tablet, the tablet includes tablet core; the tablet core comprises the pharmaceutical composition of claim 1;
wherein the active pharmaceutical ingredients in the tablet is from 1 mg/tablet to 100 mg/tablet, or is 1 mg/tablet, 2 mg/tablet, 5 mg/tablet, 10 mg/tablet, 20 mg/tablet, 30 mg/tablet, 4mg/tablet, 50 mg/tablet, or 60 mg/tablet.

12. The pharmaceutical composition according to claim 11, wherein:
when the pharmaceutical composition is in the form of tablet, the tablet includes coating materials, hydroxypropyl cellulose, hydroxypropyl methyl cellulose, ethyl cellulose, polyvinylpyrrolidone, or vinylpyrrolidone-vinyl acetate copolymer; wherein the coating is a film coat or a sugar coat, wherein the coating is in an amount from 2% to 5% of the tablet core weight.

13. The pharmaceutical composition according to claim 9, wherein:
when the pharmaceutical composition is in the form of capsule comprising the active pharmaceutical ingredient, diluents, lubricants, wherein: all of which is measured by weight:
or, the active pharmaceutical ingredient is present in an amount from 1% to 14.5%, the diluents are present in an amount from 10% to 98%, and the lubricants are present in an amount from 0.1% to 5%;
or, the active pharmaceutical ingredient is present in an amount from 1% to 14.5%, the diluents are present in an amount from 59% to 98%, and the lubricants are present in an amount from 0.5% to 3%;
or, the active pharmaceutical ingredient is present in an amount from 1% to 14.5%, the diluents are present in an amount from 80% to 98%, and the lubricants are present in an amount from 0.5% to 3%;

or, the active pharmaceutical ingredient is present in an amount from 1% to 14.5%, microcrystalline cellulose PH102 is present in an amount from 80% to 98%, and magnesium stearate is present in an amount from 0.5% to 3%;

or, the active pharmaceutical ingredient is present in an amount of 3.3%, microcrystalline cellulose PH102 is present in an amount of 95.7%, and magnesium stearate is present in an amount of 1%.

14. A preparation method of the pharmaceutical composition according to claim 1, the method comprising the following steps:
A1: Sieve the active pharmaceutical ingredient and available pharmaceutical excipients respectively;
A2: Sieve the active pharmaceutical ingredient and part of the diluents to get the mixture;
A3: Add the remaining diluents into the mixture of Step A2 and sieve to get the mixture;
A4: Pellet the mixture of step A3 to get particles;
A5: Sieve and pelletize the particles of Step A4 and lubricants;
A6: Press and pack;
or comprising the following steps:
B1: Sieve the active pharmaceutical ingredient, diluents and disintegrating agents, the internal added lubricants and external added lubricants;
B2: Mix the active pharmaceutical ingredient and diluents to get premix 1, sieve premix 1, sieve disintegrants and remaining diluents to wash the machine, and mix with the screened premix 1, Sieve the mixture twice again to get premix 2;
B3: Mix premix 2 with internal added lubricant to get premix 3;
B4: Pellet premix 3 to get particles, mix the particles with external added lubricant to get premix 4;
B5: Press premix 4 and then pack; or pellet premix 4, and then press and pack.

15. A preparation method according to claim 14, wherein in step A1, the active pharmaceutical ingredient is to sieve with 200 meshes;
and/or, in step A1, the available pharmaceutical excipients are to use from 40 meshes to 100 meshes to sieve;
and/or, in step A2, the sieving is with 40 meshes;
and/or, in step A2, the times of the sieving are from 5 to 15 times;
and/or, in step A2, food additives and/or disintegrating agents are added to sieve together;
and/or, in step A3, the sieving is with 40 meshes;
and/or, in step A3, the times of the sieving are from 5 to 15 times;
and/or, in step A4, the method of pelleting is to use dry granulation;
and/or, in step A5, the sieving is with 24 meshes;
and/or, in step A5, the times of the sieving are from 5 to 15 times;
and/or, in step A5, the method of pelleting is to use dry granulation;
and/or, in step A5, the disintegrating agents are added to sieve together;
and/or, in step A6, the method of pressing is to use Φ5.0 mm flat concave die;
and/or, in step A6, the method of pressing is with hardness from 30N to 70N;
and/or, in step B1, the active pharmaceutical ingredient is to use ball mill or microgrinder to smash, more microgrinder;

and/or, in step B1, the active pharmaceutical ingredient, diluents and disintegrating agents is to use 20 meshes to sieve;

and/or, in step B1, the inners and outer lubricants is to use 60 meshes to sieve;

and/or, in step B2, the active pharmaceutical ingredients mixing with the diluents, the diluents are to use 2 times of the active pharmaceutical ingredients;

and/or, in step B2, the active pharmaceutical ingredients mixing with the diluents, and the mixing is in a barrel mixer;

and/or, in step B2, the sieving is to use Comil;

and/or, in step B3, mix premix 2 with internal added lubricant, the mixing is in a mixing drum;

and/or, in step B4, pellet premix 3 to get particles, the pelleting is in a roller pelleting machine;

and/or, in step B4, the pelleting is to use dry granulation;

and/or, in step B4, mix the particles with external added lubricant, and the mixing is in a barrel mixer;

and/or, in step B4, take samples to detect the mixing uniformity, LOD, particle size distribution, etc. after the end of mixing.

16. A preparation method of claim 14, wherein when the pharmaceutical composition is in the form of a capsule, the method comprises the following steps:

C1: Sieve the active pharmaceutical ingredient and available pharmaceutical excipients respectively;

C2: Sieve the active pharmaceutical ingredients and part of the diluents to get the mixture;

C3: Add the remaining diluents into the mixture of step C2 in several times, then sieve to get the mixture;

C4: Sieve the mixture of C3 and lubricants to get the mixture;

C5: Fill the C4 mixture into the capsule and pack.

17. A preparation method according to claim 16, wherein in step C1, the active pharmaceutical ingredient is to use 40 meshes to sieve;

And/or, in step C2, the sieving is with 40 meshes;

And/or, in step C2, the times of the sieving are from 5 to 15 times;

And/or, in step C3, the sieving is with 40 meshes;

And/or, in step C3, the times of the sieving are from 5 to 15 times;

And/or, in step C4, the sieving is with 40 meshes;

And/or, in step C4, the times of the sieving are from 5 to 15 times.

18. A method for treating of tumors in a patient, comprising administration to the patient in need thereof a therapeutic effective amount of the pharmaceutical composition according to claim 1, wherein the tumors are selected from leukemia, gastrointestinal stromal tumors, histiocytic lymphoma, non-small cell lung cancer, small cell lung cancer, lung adenocarcinoma, lung squamous cell carcinoma, pancreatic cancer, breast cancer, liver cancer, skin cancer, epithelial cell cancer, prostate cancer, and nasopharyngeal cancer.

* * * * *